(12) United States Patent
Creux et al.

(10) Patent No.: US 9,841,388 B2
(45) Date of Patent: Dec. 12, 2017

(54) X-RAY TOMOGRAPHY DEVICE

(75) Inventors: Patrice Creux, Lescar (FR); Gérald Hamon, Pau (FR)

(73) Assignees: TOTAL SA, Courbevoie (FR); UNIVERSITE DE PAU ET DES PAYS DE L'ADOUR, Pau (FR)

( * ) Notice: Subject to any disclaimer, the term of this patent is extended or adjusted under 35 U.S.C. 154(b) by 527 days.

(21) Appl. No.: 14/123,018

(22) PCT Filed: Jun. 1, 2012

(86) PCT No.: PCT/EP2012/060440
§ 371 (c)(1),
(2), (4) Date: Nov. 27, 2013

(87) PCT Pub. No.: WO2012/164091
PCT Pub. Date: Dec. 6, 2012

(65) Prior Publication Data
US 2014/0133623 A1    May 15, 2014

Related U.S. Application Data (60) Provisional application No. 61/492,272, filed on Jun. 1, 2011, provisional application No. 61/492,268, filed on Jun. 1, 2011.

(51) Int. Cl.
*G01N 23/04* (2006.01)

(52) U.S. Cl.
CPC ..... *G01N 23/046* (2013.01); *G01N 2223/419* (2013.01)

(58) Field of Classification Search
CPC ........... G01N 2223/419; G01N 23/046; G01N 15/08; G01N 23/04; A61B 6/032; A61B 6/542
(Continued)

(56) References Cited

U.S. PATENT DOCUMENTS

| 4,635,197 A * | 1/1987 | Vinegar | G06T 11/005 |
|---|---|---|---|
| | | | 250/361 R |
| 4,688,238 A * | 8/1987 | Sprunt | G01N 23/046 |
| | | | 378/210 |

(Continued)

FOREIGN PATENT DOCUMENTS

| DE | 196 28 675 A1 | 1/1998 |
|---|---|---|
| DE | 10 2008 011 301 A1 | 9/2009 |

(Continued)

OTHER PUBLICATIONS

International Search Report for International Application No. PCT/EP2012/060441 dated Jul. 23, 2012.
(Continued)

*Primary Examiner* — Wyatt Stoffa
(74) *Attorney, Agent, or Firm* — Patterson Thuente Pedersen, P.A.

(57) ABSTRACT

An X-ray tomography device for providing a 3D image of a sample comprising a X-ray source, a cell, a photon detector and a processing unit. The processing unit computes the 3D tomography image on the basis of the acquired images corresponding to a plurality of cell angles. The cell is positioned so as the photon detector senses mainly photons coming from the sample inside the cell, and the photon detector is overexposed to cancel pixels corresponding to photons not coming from the sample.

20 Claims, 4 Drawing Sheets

(58) Field of Classification Search
USPC .......................................................... 378/19
See application file for complete search history.

(56) References Cited

U.S. PATENT DOCUMENTS

| | | | |
|---|---|---|---|
| 5,063,509 A * | 11/1991 | Coles ................... | G01N 23/046 250/269.1 |
| 5,164,590 A * | 11/1992 | Coles ................... | G01N 23/046 250/253 |
| 5,287,396 A * | 2/1994 | Stegehuis ............... | A61B 6/06 378/151 |
| 5,635,138 A | 6/1997 | Amatucci et al. | |
| 5,812,629 A | 9/1998 | Clauser | |
| 5,892,808 A * | 4/1999 | Goulding ............. | G01N 23/046 378/58 |
| 6,035,015 A | 3/2000 | Ruth et al. | |
| 6,687,333 B2 * | 2/2004 | Carroll .................... | H05G 2/00 378/119 |
| 6,839,402 B2 | 1/2005 | Stabe et al. | |
| 7,050,533 B2 | 5/2006 | Heismann et al. | |
| 7,130,375 B1 | 10/2006 | Yun et al. | |
| 7,471,768 B2 | 12/2008 | Curtis et al. | |
| 7,684,540 B2 | 3/2010 | Groves et al. | |
| 7,924,973 B2 | 4/2011 | Kottler et al. | |
| 8,068,579 B1 * | 11/2011 | Yun ...................... | G01N 23/046 378/21 |
| 8,073,099 B2 | 12/2011 | Niu et al. | |
| 8,565,371 B2 | 10/2013 | Bredno | |
| 8,755,487 B2 | 6/2014 | Kaneko et al. | |
| 9,084,528 B2 | 7/2015 | Geller et al. | |
| 2005/0286680 A1 | 12/2005 | Momose | |
| 2007/0183581 A1 | 8/2007 | Heismann et al. | |
| 2009/0092227 A1 | 4/2009 | David et al. | |
| 2009/0128230 A1 | 5/2009 | Roh et al. | |
| 2009/0128830 A1 | 5/2009 | Kottler et al. | |
| 2009/0143885 A1 * | 6/2009 | Grant ..................... | B23H 1/00 700/97 |
| 2009/0316857 A1 * | 12/2009 | David .................... | A61B 6/484 378/62 |
| 2010/0080341 A1 * | 4/2010 | Popescu ................ | A61B 6/032 378/19 |
| 2010/0220834 A1 * | 9/2010 | Heismann .............. | A61B 6/032 378/19 |
| 2010/0301458 A1 | 12/2010 | Sewell et al. | |
| 2012/0041679 A1 | 2/2012 | Stampanoni et al. | |
| 2012/0128119 A1 * | 5/2012 | Notohara ............... | A61B 6/025 378/10 |
| 2012/0236985 A1 | 9/2012 | Schusser et al. | |
| 2013/0094625 A1 * | 4/2013 | Huang ................... | A61B 6/484 378/6 |
| 2014/0086385 A1 | 3/2014 | Creux et al. | |
| 2014/0105353 A1 | 4/2014 | Pfeiffer et al. | |
| 2014/0112440 A1 * | 4/2014 | David .................. | A61B 6/4035 378/62 |

FOREIGN PATENT DOCUMENTS

| | | |
|---|---|---|
| GB | 2 185 144 A | 7/1987 |
| GB | 2185114 | 7/1987 |
| WO | WO 2006 131235 A1 | 12/2006 |

OTHER PUBLICATIONS

International Search Report for International Application No. PCT/EP2012/060440 dated Jul. 24, 2012.

International Search Report for International Application No. PCT/EP2012/060439 dated Jul. 23, 2012.

Kak et al., "Principles of Computerized Tomographic Imaging", IEEE Press, 1988.

Bech, Martin, "X-ray imaging with a grating interferometer", Ph.D. Thesis, Faculty of Science, University of Copenhagen, May 2009, 121 pages.

Herzen, Julia, "A grating interferometer for materials science imaging at a second-generation synchrotron radiation source", Vom Department Physik der Universitat Hamburg im Jahr 2010 als Disssertation angenommene Arbeit, Ph.D. Thesis, HZG Report Feb. 2011, 112 pages.

Application and File History for U.S. Appl. No. 14/123,000, filed Nov. 27, 2013 inventors Creux et al.

Application and File History for U.S. Appl. No. 14/123,031, filed Nov. 27, 2013 inventors Pfeiffer et al.

Karagodsky, Vadim et al., "High efficiency x-ray source based on inverse Compton scattering in an optical Bragg structure", *Plasma Physics and Controlled Fusion, IOP Publishing*, vol. 53, No. 1, Dec. 16, 2010, pp. 1-10.

Meyer, V. Et al., "Gas Bubble Nucleation of Extra-Heavy Oils in Porous Media: A New Computerized Tomography Technique and Physical Approach", Society of Petroleum Engineers, SPE-110468-PP, Nov. 11-14, 2007, pp. 1-7.

Sachse, Alexander et al., "Functional silica monoliths with hierarchical uniform porosity as continuous flow catalytic reactors", Microporous and Mesoporous Materials, El Sevier, Oct. 26, 2010, pp. 1-11.

* cited by examiner

X-RAY TOMOGRAPHY DEVICE

PRIORITY CLAIM

The present application is a National Phase entry of PCT Application No. PCT/EP2012/060440, filed Jun. 1, 2012, which claims priority from U.S. Provisional Patent Application No. 61/492,272, filed Jun. 1, 2011, and U.S. Provisional Patent Application No. 61/492,268, filed Jun. 1, 2011, said applications being hereby incorporated by reference herein in their entirety.

FIELD OF THE INVENTION

The present invention concerns an X-ray tomography device.

BACKGROUND OF THE INVENTION

The present invention concerns an X-ray tomography device adapted to petrophysics application, such as to study the flow of fluids into a porous medium. For example, the aim is to study the multiphase flow of a mix of two or three fluids inside a porous medium: a mix of any two of water, gas and oil or the three of them.

The known X-ray tomography systems are adapted to study the morphology of rock pores, to identify the minerals comprised into the rock sample (the porous medium) or the topology of various fluid phases present in the rock sample under static (ie non flowing) conditions.

Because of the 3D image reconstruction process included in these devices, the acquired images taken by a photon detector embrace the entire cell to have as much information as possible according to a spatial point of view.

In case, the region of interest is a small part of the cell, the 2D images acquired by the photon detector and the 3D tomography images calculated after reconstruction have a limited number of useful pixels.

Therefore, other known methods require stitching a lot of radiographies, and to reconstruct more data and to work on very large images for the 3D image treatment. These methods are acquisition time and calculation time consuming.

OBJECTS AND SUMMARY OF THE INVENTION

One object of the present invention is to provide an X-ray tomography device that can be used to analyse flow of fluids inside a porous medium, such as a rock sample of a geological formation. It is needed an X-ray tomography device having an improved image quality for this field of use.

To this effect, the X-ray tomography device according to the invention is adapted for providing a 3D tomography image of a sample, and it comprises:
- a X-ray source emitting a photon beam in the direction of a beam axis,
- a cell adapted to include a porous sample to be imaged, said cell being situated inside the photon beam and being able to rotate about a cell angle around a cell axis that is substantially perpendicular to the beam axis, and being adapted to enable the porous sample to be flooded by at least one fluid,
- a photon detector receiving a transmitted photon beam that is transmitted through said cell, said photon detector providing at least one acquired image for each angle of a plurality of cell angles, and
- a processing unit that computes the 3D tomography image on the basis of the acquired images corresponding to the plurality of cell angles.

The device further comprises following features:
- the cell is positioned inside the photon beam so as each acquired image produced by the photon detector comprises at least 70% of pixels corresponding to the sample, and
- the photon detector is exposed to the photon beam for each acquired image during an exposure length of time higher than a first time limit and lower than a second time limit, said first time limit being determined so as the pixels not corresponding to the sample are overexposed, and the second time limit being determined so as the pixels corresponding to the sample are not overexposed.

Thanks to these features, the X-ray tomography device is able to get acquired images and to compute a 3D tomography image of the sample having an optimized acquisition sequence to reduce the acquisition time for the highest reachable resolution (high number of pixels or voxels). These images are more accurate and it is possible to have local and global views of the sample. Therefore, the porous medium and the fluid flow in the porous medium of the sample can be studied at the same time at a large or reduced scale.

In various embodiments of the X-ray tomography device, one and/or other of the following features may optionally be incorporated.

According to an aspect, the cell comprises an outer casing made of a material having an X-ray transmission higher than 80%.

According to an aspect, the cell comprises an outer casing being able to withstand to a pressure higher than 300 bars, and preferably up to 1000 bars.

According to an aspect, the cell comprises an outer casing being able to withstand to a temperature higher than 300° C., and preferably up to 650° C.

According to an aspect, the X-ray source is a monochromatic source, and preferably a compact light source using a collision between a laser beam and an opposing electron beam.

According to an aspect, the processing unit is computing the 3D tomography image during a time period lower than an acquisition length of time used for producing the acquired images corresponding to the plurality of cell angles.

According to an aspect, the cell has a size comprised in the range of 0.3 cm to 20 cm, and preferably in the range of 0.6 cm to 10 cm.

According to an aspect, the casing of the cell is made of a material in a list comprising the beryllium, the beryllium alloy, and a carbon-carbon composite.

According to an aspect, the photon detector comprises a CCD of at least ten megapixels.

According to an aspect, the X-ray tomography device further comprises a grating based interferometer situated between the cell and the photon detector.

According to an aspect, the X-ray tomography device further comprises a microscope situated between the cell and the photon detector.

BRIEF DESCRIPTION OF THE DRAWINGS

Other features and advantages of the invention will be apparent from the following detailed description of one of its embodiments given by way of non-limiting example, with reference to the accompanying drawings. In the drawings.

DETAILED DESCRIPTION OF THE DRAWINGS

In the various figures, the same reference numbers indicate identical or similar elements. The direction Z is a vertical direction. A direction X or Y is a horizontal or lateral direction. These are indications for the understanding of the invention.

Figure 1:
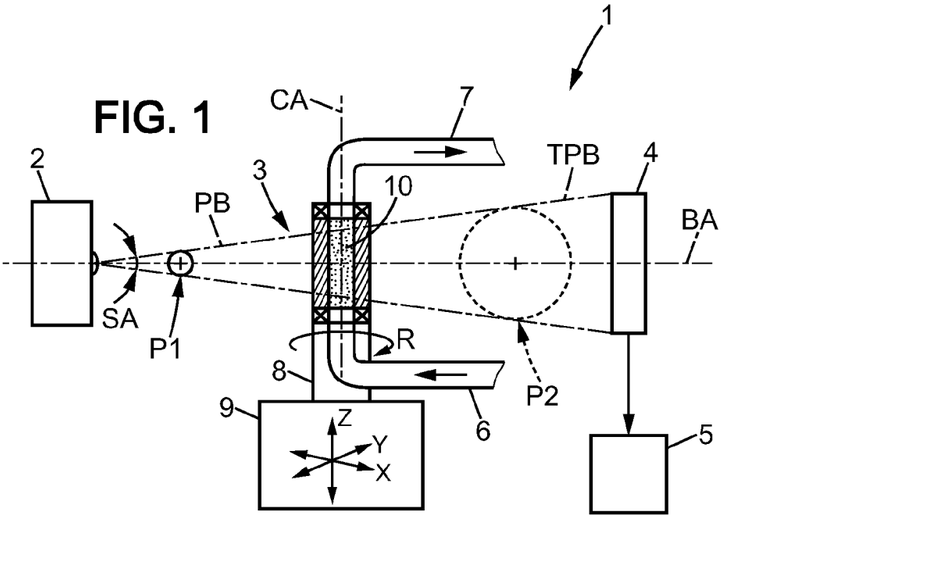
FIG. 1 is a schematic view of a X-ray tomography device according to the invention.

The X-ray tomography device 1 shown on the FIG. 1 comprises:
- a X-ray source 2 emitting a photon beam PB in the direction of a beam axis BA,
- a cell 3 comprising a porous sample 10 to be imaged,
- a photon detector 4 receiving a transmitted photon beam TPB that is transmitted through said cell 3, and
- a processing unit 5 computing the 3D tomography image on the basis of the acquired images provided by the photon detector 4.

The X-ray source 2 may be monochromatic or polychromatic source (synchrotron, lab x-ray source or table top synchrotron), so that the cell may be illuminated with very different levels of brilliance. The polychromatic sources spread their energy into a wide frequency bandwidth. It is possible to filter the photon beam PB to have a quasi-monochromatic photon beam. However, this decreases a lot the photon flux. The monochromatic source concentrates the energy on a very narrow frequency bandwidth. The length of time needed by a detector for acquiring an image is then low therefore non compatible with multiphase flow tracking The photon beam PB generated by said X-ray source 2 is a diverging cone beam having a solid angle SA that is wide, and for example higher than 0.1 degree or a few mrad around the beam axis BA. It is possible to illuminate a complete cell having a size of 10 cm at a distance from the X-ray source 2 that is a small distance, for example lower than 25 m, and preferably lower than 10 m. The solid angle SA may be higher than 0.5 degree.

Preferably, the X-ray source is able to emit a photon beam having a high level of energy, for example comprised between 10 and 200 KeV. The photon flux may be higher than $10^8$ photons/s near the photon detector 4, and preferably higher than $10^{11}$ photons/s. The device is then able to image thick cells and thick samples (between 0.3 cm and 10 cm). The X-ray source may have a tuneable X-ray energy level.

For example, the X-ray source 2 may be a compact photon source using collision between a laser beam and an opposing electron beam. Such X-ray source 2 preferentially uses Inverse Compton Effect (Thomson scattering) to generate a natural monochromatic photon beam PB having a high level of energy. The main advantage of such X-ray sources is that they are very compact compared to classical synchrotron devices. Known Table-top synchrotron device using such physical properties are the "Compact Light Source" (CLS) from Lyncean Technologies Inc., but filtering very brilliant polychromatic flux such "Mirrorcle" from Photon Production Lab may produce a quite similar result.

The X-ray source 2 may be tuneable according to the energy level (brilliance) so as to proceed to various experiments above the porous sample.

The cell 3 is situated inside the photon beam PB. The cell position can be controlled via a rotation mean 8 (Z rotation) and a translation mean 9 (XYZ translations).

Thanks to the rotation mean 8, the cell 3 can be rotated around a cell axis CA substantially parallel to axis Z and perpendicular to the X axis, the beam axis BA on FIG. 1. The cell 3 is rotated of a cell angle around the cell axis CA. The detector 4 can then provide images from the cell (sample) from various view angles and the processing unit 5 can compute a 3D tomography image of the sample.

Thanks to the translation mean 9, the cell 3 can be positioned inside the photon beam PB.

The cell 3 can be placed or positioned between a first distance from the source 2 and a second distance from the source 2. The first distance may be short and the cell 3 is close to the X-ray source 2 (see position P1 on FIG. 1). This configuration optimizes the maximal flux in high resolution (stitching mode or local tomography). The second distance is much higher than the first distance, the cell 3 being away from the X-ray source 2. In this configuration, it is possible to illuminate the whole region of interest permitting to easily switch from a global tomography mode to local tomography based on observed changes induced by the multiphase flow. The acquisition time in this last configuration is less performing than the first one but it permits to analyse the sample in interactive mode For example, the cylindrical rock sample contained inside the cell 3 has a size comprised in the range of 0.3 cm to 10 cm. The size is preferably in the range 0.6 cm to 3 cm in diameter and in the range of 2 cm to 10 cm in length. The size of the rock sample is chosen big enough to study multiphase transport properties at a scale representative of macroscopic transport properties in the said rock and small enough to enable high resolution tomography of the sample in a length of time that allows imaging the whole sample in less than ten minutes: acquiring the images from the plurality of cell angles within said length of time.

The cell 3 is for example a tube extending along the cell axis CA, said tube receiving the sample of porous medium. The cell 3 comprises an input conduct 6 that input the fluid to the cell 3 and an output conduct 7 that outputs the fluid from the cell. The cell is adapted to be crossed by the fluid.

The X-ray tomography device 1 also comprises hydraulic devices to provide the fluid to the input conduct and to get back this fluid from the output conduct. These hydraulic devices can also add physical conditions to the fluid: temperature, pressure. To this end, these hydraulic devices include a thermal regulator, and a pressure regulator. The sample 10 inside the cell 3 can be tested according to the physical conditions of the geologic formation.

The thermal regulator can heat the sample up to a temperature of 650° Celsius.

The pressure regulator can pressurize the sample up to a pressure of 1000 bars.

The cell 3 is a sort of Hassler cell meeting the requirements of X-ray tomography imaging. The cell 3 is adapted to enable the porous sample 10 to be flooded by one or several fluids under controlled pressure and temperature conditions.

The cell 3 is made of a material that is transparent to the X-ray photon beam. Advantageously, it is made of beryllium, or beryllium alloy such beryllium aluminium alloy, or a carbon-carbon composite.

The photon detector 4 can be tuned to have a sensitivity corresponding to the sample and fluids. Small variations of fluid densities can be therefore detected. Oil and water can be distinguished in the acquired images provided by the photon detector 4 using very fast classical absorption mode, or phase mode or dark field mode.

The photon detector 4 is providing at least one image for each angle of a plurality of cell angles. All these acquired images are taken during a length of time lower than ten minutes for the whole volume to analyse. It is assumed that the state of the sample does not change much during this length of time: the fluid movements inside the porous medium remain very small. All the acquired images from various cell angles are then supposed to represent a unique state of the sample.

Advantageously, the length of time is lower than one minute. The images represent more precisely a unique state of the sample, and the tomography device is acquiring images in real time and stores all these images for the processing unit 5.

The photon detector 4 can be a flat panel, or an X-ray CCD (Charge-Coupled Device) or a CMOS. The photon detector 4 has a high resolution. It is for example a CCD having at least ten megapixels. The acquired images are enough accurate to visualise at the same time (simultaneously) the complete field of view of the sample or very small details inside the sample thanks to a stitching mode or local tomography process. In this way several ways are possible to scan the sample, and the acquired image can be taken in a very short length of time and the acquired image is enough exposed to photon flux to show small details and small variations of densities.

The processing unit 5 is computing the 3D tomography image on the basis of the acquired images corresponding to the plurality of cell angles. Such reconstruction method is known and efficient (fast and providing a very good image quality) benefiting from the quasi parallel approximation. Examples of reconstruction methods can be found in the following document:

A. C. Kak and Malcolm Slaney, *Principles of Computerized Tomographic Imaging*, IEEE Press, 1988.

In the present invention, the processing unit 5 may comprise parallel computing means so that the 3D tomography image can be computed during a very short time period. This high performance for reconstruction time and imaging are mainly due to the quasi parallel beam geometry. The time period can be lower than the length of time for acquiring the images from various cell angles of the sample. The X-ray tomography device is therefore generating real time 3D tomography images, and can visualize a real time movie showing the fluids movements inside the porous medium.

Figure 5:
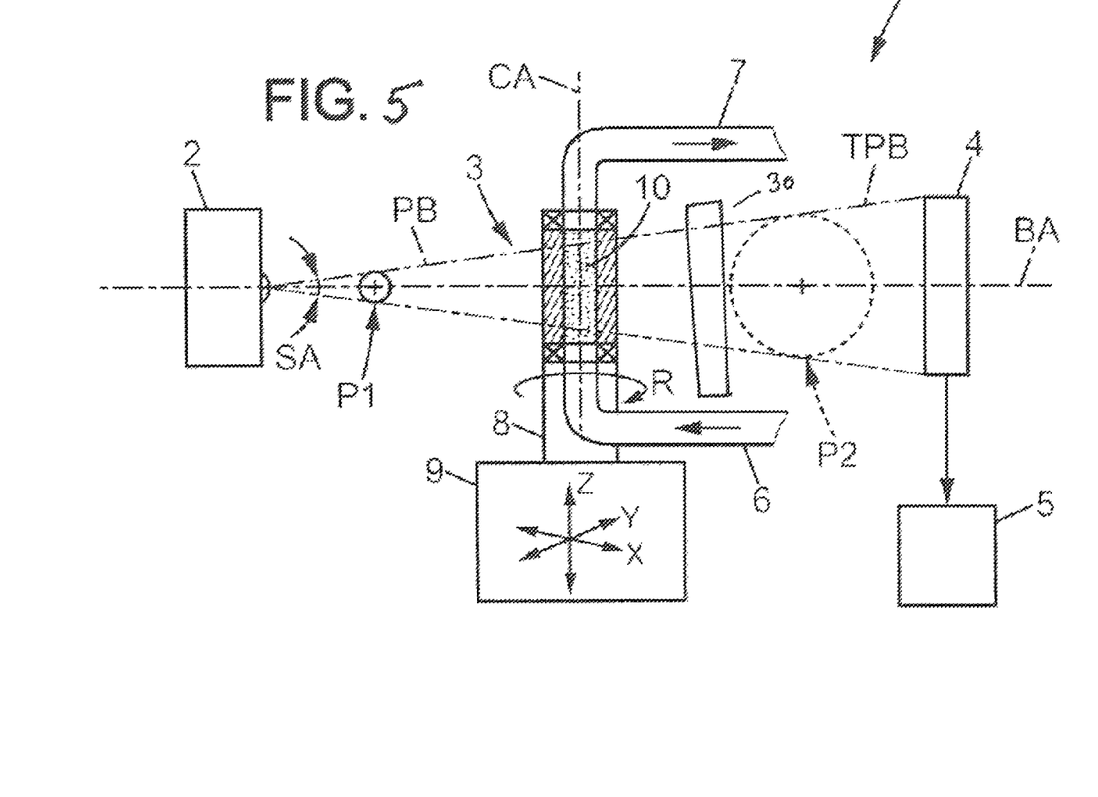
FIG. 5 is a schematic view of a X-ray tomoraphy device according to the invention with a microscope.
Figure 6:
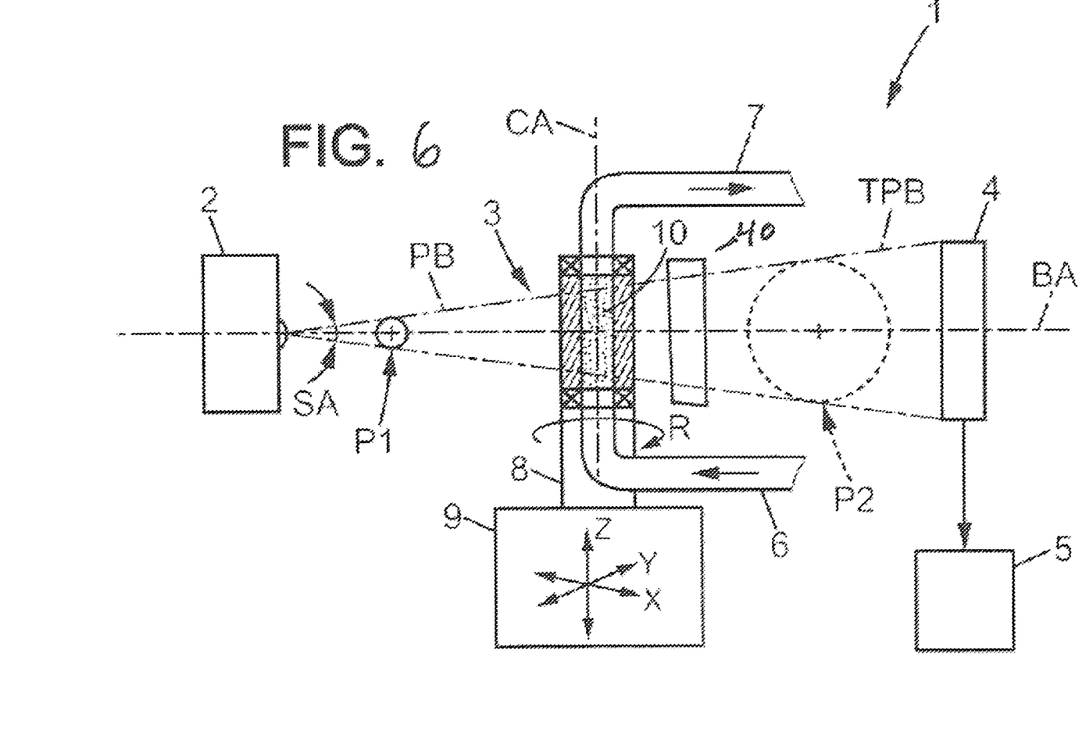
FIG. 6 is a schematic view of a X-ray tomography device according to the invention with a grafting based interferometer.

The tomography device 1 may comprise a microscope 30 to obtain high (accurate) resolutions as shown in FIG. 5. In that case, the resolution may reach 200 nm of voxel size which is the theoretical limit of microscopes due to Rayleigh criterion, The tomography device 1 may also comprise a grating based interferometer 40, situated between the cell 3 and the microscope or the photon detector 4 as shown in FIG. 6. Such gratings improve the 15 contrast of the acquired images by adding absorption contrast image, phase contrast image and dark field contrast image: materials having similar densities can be distinguished on the acquired images by photon detector 4, In that case, the same resolution than obtained only by the microscope can be obtained.

The gratings, the microscope and the detector 4 compose an optical station of the X-ray tomography device 1.

Figure 2:
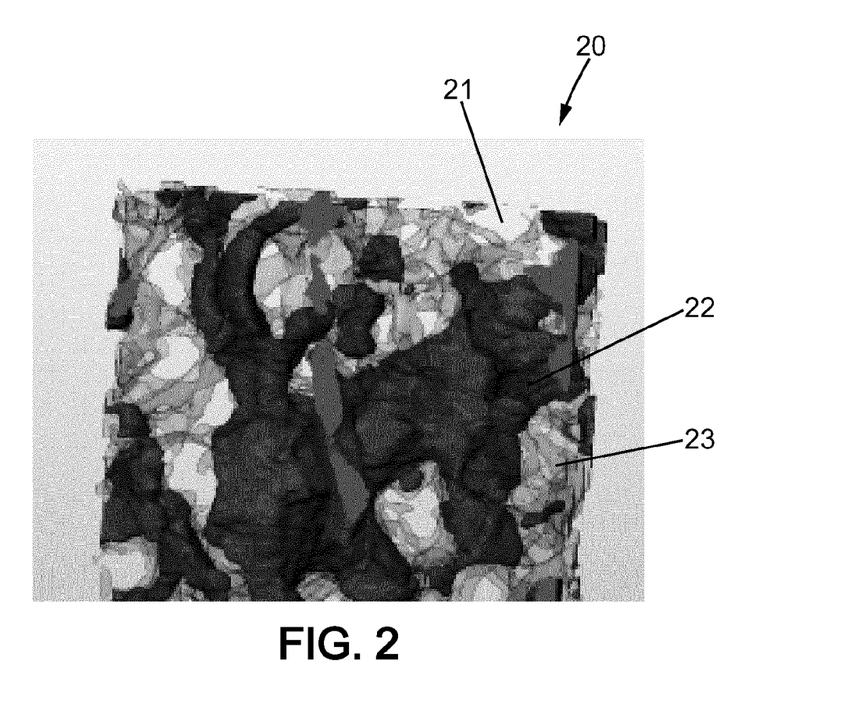
FIG. 2 is an example of a 3D tomography image provided by the device of FIG. 1.

The FIG. 2 is showing an example of a projection of 3D image 20 provided by the X-ray tomography device 1 of the invention. The 3D tomography image comprises various gray levels or various colours, each representing a constituent of the sample. The reference 21 represents the porous medium. The reference 22 represents a first fluid having a first density. The reference 23 represents a second fluid having a second density.

Figure 3:
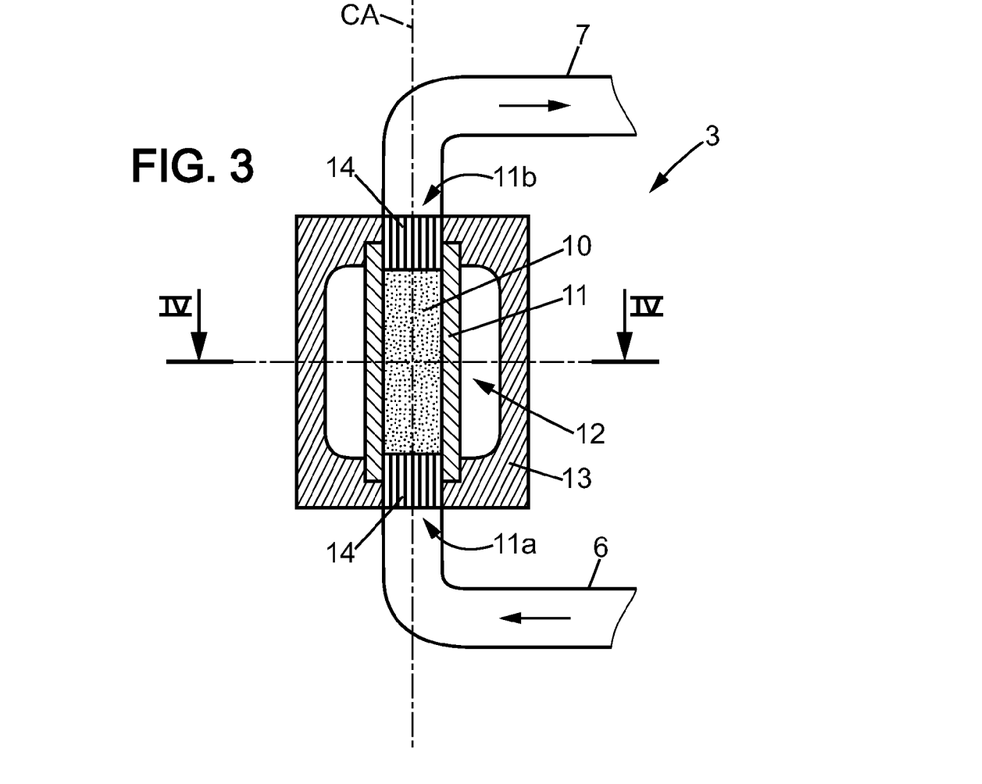
FIG. 3 is a detailed schematic view according to a longitudinal cut of the sample 15 cell comprised in the X-ray tomography device of FIG. 1.
Figure 4:
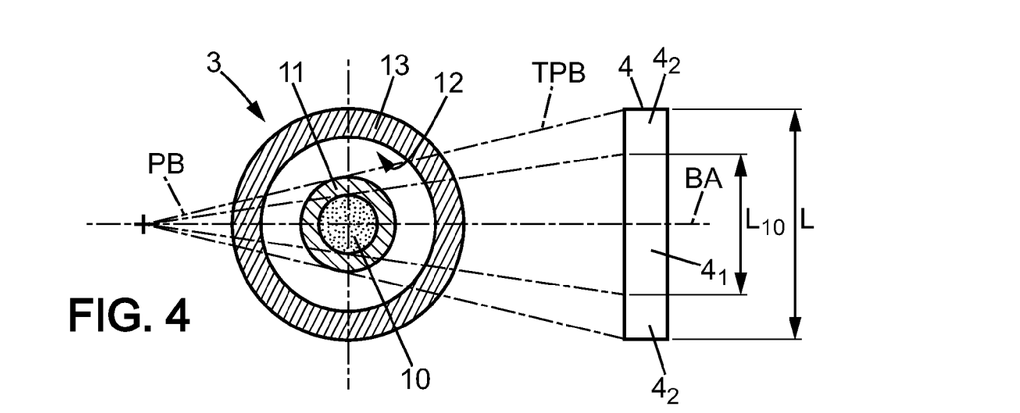
FIG. 4 is a transversal cut view of the sample cell of FIG. 3.

The cell 3 will now be more precisely described in view of the FIGS. 3 and 4.

The cell 3 has an elongated and generally cylindrical shape according to the cell axis CA. It comprises a first cavity comprising the cell axis CA, said first cavity being filled up with the rock sample 10 (porous medium). It basically adopts the mechanical design of a Hassler type cell, but the nature of the used materials is different so that it is transparent to X-ray beam to reach high resolution X-ray tomography.

The cell 3 is made of materials with specific X-ray properties but working under high pressure and high temperature conditions (up to the above cited conditions). Such cell 3 requires higher material thicknesses than for lower pressures to be able to resist to the stresses. The present invention is therefore more important when working with high pressure and high temperature conditions.

The porous medium 10 is surrounded by a sealing tube 11 having and input port 11a and an output port 11b. The input and output ports 11a, 11b can be equipped with diffusers 14 adapted to canalise the fluid in the direction of the cell axis CA at the input and output of the first cavity.

The cell 3 also comprises a second cavity 12 surrounding the sealing tube 11. Said second cavity 12 is fed with a control fluid that impose pressure and temperature to said cavity. The sealing tube 11 is for example made of stainless steel or high performing polymers. This sealing tube 11 is transmitting the pressure and temperature from the control fluid to the sample 10 inside the first cavity.

The cell 3 then comprises an outer casing 13 that surrounds the second cavity 12 and closes its ends in the longitudinal cell axis direction. This outer casing 13 must withstand the pressure and temperature conditions imposed by the control fluid inside the second cavity 12.

The cell casing 13, the control fluid inside the second cavity 12 and the sealing tube 11 are made of low X-ray absorbing materials (high level of X-ray transmission material).

Usually, polymeric materials are used in X-ray tomography devices. But, these polymeric materials cannot withstand the physical conditions imposed by the control fluid. In the present invention, the outer casing 13 is preferably made of beryllium, or beryllium alloy (for example a beryllium aluminium alloy), or a carbon-carbon composite. But, other materials may be used if they have an X-ray transmission higher than 80% and preferably higher than 90% inside the photon energy bandwidth of 10 keV to 200 keV.

Thanks to this first feature, the material of the outer casing 13 has a low effect on the image taken by the photon detector 4: The 2D acquired images and the 3D tomography images are less affected by the casing material, and these images are more contrasted. It is possible to distinguish elements or fluids inside the sample that have very close densities, such as water, oil and brine.

The cell casing 13, the control fluid inside the second cavity 12 and the sealing tube 11 are also preferably made of a homogeneous material so as the various images from various cell angles are not affected and not noisy because of non homogeneities.

The cell 3 of the present invention is also preferably positioned inside the photon beam PB according to the view of FIG. 4 so as the photon detector 4 is mainly illuminated via the sample 10. The cell 3 is positioned near the X-ray source.

The X-ray photon beam PB is crossing the cell 3 and the transmitted photon beam TPB is projected above the photon detector 4, said photon detector 4 providing an image corresponding to said transmitted photon beam PB to produce an image. The portion of the photon beam PB crossing the sample 10 is illuminating a central portion $4_1$ of the photon detector, and reciprocally is not illuminating lateral portions $4_2$ of the photon detector. Said central portion $4_1$ has a width $L_{10}$ on the FIG. 4, and the photon detector has itself a width L.

The cell 3 is then positioned so as the ratio $L_{10}/L$ is higher than 0.7, meaning that at least 70% of the pixels in the image from the photon detector 4 correspond to sensitive elements inside the photon detector receiving transmitted photons that have crossed the sample 10.

Thanks to this second feature, the image of the sample is more accurate.

The photon detector 4 is composed of a matrix of sensitive elements that are counting receiving photons (each X-ray photon is usually converted into an electron via a scintillator element).

These sensitive elements may have an anti-blooming functionality: Each of them deliver a pixel value that is saturated to a maximum value if the counted number of photon is higher than a maximum limit.

The photon detector 4 is overexposed: It is exposed to the transmitted photon beam TPB during an exposure length of time higher than a first time limit. The first time limit is determined so as the sensitive elements receiving photons that have not crossed the sample 10 have reached said maximum value (blooming saturation) corresponding to 100% transmission.

The photon detector 4 is not too much overexposed: The exposure length of time is lower than a second time limit more realistically a few tenths of seconds. The second time limit is determined so as the sensitive elements receiving photons that have crossed the sample 10 have not reached said maximum value (blooming saturation).

Thanks to this third feature, the acquired image is weakly overexposed and it cancels the informations in the acquired image corresponding to the cell casing 13, the control fluid inside the second cavity 12 and the sealing tube 11 that are not relevant.

The optical station is fitted around the region of interest to avoid a strong blooming due to direct X-ray exposure or to the highest thickness of the cell 3 which is the thicker and therefore the most attenuating zone.

These elements have therefore low effect on the acquired image provided by the photon detector 4: the acquired image is again more contrasted.

Contrary to what was expected, the inventors have discovered that the second and third features (reduced field of view and over exposition of acquired image) are not disturbing the following reconstruction computations for calculating the 3D tomography image.

The prior art X-ray tomography devices are usually acquiring a complete field of view and acquiring non over-exposed images to compute a 3D tomography image. It is expected reconstruction problems if it is not done in that manner.

One benefit of present invention is to optimize the use of the photon detector 4 to useful region of interest. The whole pixels of the photon detector are used in the useful area.

However, in the case of geological or petrophysical porous sample analysis it was found that these known and usual uses of an X-ray tomography device are not relevant.

Thanks to this property, there are significant progresses in acquisition time which is quite decisive to image a multi-phase flow but also in the reconstruction and image treatment processes. Considering the outer diameter of the region of interest (the sample 10) and the outer diameter of the cell 3, the benefit in acquisition time is given by the ratio of the integer number of necessary stitching steps to acquire the whole outer diameter of the cell 3 divided by the integer number of necessary stitching steps to acquire the whole outer diameter of the sample 10.

Then, the size of the data set changes with a law of this square number. This is a great improvement for reducing the time spent to compute the 3D tomography image.

The embodiments above are intended to be illustrative and not limiting. Additional embodiments may be within the claims. Although the present invention has been described with reference to particular embodiments, workers skilled in the art will recognize that changes may be made in form and detail without departing from the spirit and scope of the invention.

Various modifications to the invention may be apparent to one of skill in the art upon reading this disclosure. For example, persons of ordinary skill in the relevant art will recognize that the various features described for the different embodiments of the invention can be suitably combined, un-combined, and re-combined with other features, alone, or in different combinations, within the spirit of the invention. Likewise, the various features described above should all be regarded as example embodiments, rather than limitations to the scope or spirit of the invention. Therefore, the above is not contemplated to limit the scope of the present invention.

The invention claimed is:

1. An X-ray tomography device for providing a 3D tomography image of a sample, said device comprising:
   a X-ray source emitting a photon beam in the direction of a beam axis,
   a cell adapted to include a porous sample to be imaged, said cell being situated inside the photon beam and being able to rotate about a cell angle around a cell axis that is substantially perpendicular to the beam axis, and being adapted to enable the porous sample to be flooded by at least one fluid,
   a photon detector receiving a transmitted photon beam that is transmitted through said cell, said photon detector providing at least one acquired image for each angle of a plurality of cell angles, and
   a processor that computes the 3D tomography image on the basis of the acquired images corresponding to the plurality of cell angles,
   wherein
   the X-ray tomography device further comprises a mean for positioning the cell inside the photon beam so as each acquired image produced by the photon detector comprises at least 70% of pixels corresponding to the sample,
   the processor controls an exposure length of time of the photon detector in the photon beam for each acquired image so as the exposure length of time is higher than a first time limit and lower than a second time limit, said first time limit being determined so as the pixels not corresponding to the sample are overexposed, and the second time limit being determined so as the pixels corresponding to the sample are not overexposed, and the processor computes the 3D tomography image for a region of interest with the non overexposed pixels and with the overexposed pixels.

2. The X-ray tomography device according to claim 1, wherein the cell comprises an outer casing made of a material having an X-ray transmission higher than 80%.

3. The X-ray tomography device according to claim 1, wherein the cell comprises an outer casing being able to withstand to a pressure higher than 300 bars.

4. The X-ray tomography device according to claim 1, wherein the cell comprises an outer casing being able to withstand to a temperature higher than 300° C.

5. The X-ray tomography device according to claim 1, wherein the X-ray source is a monochromatic source, and preferably a compact light source using a collision between a laser beam and an opposing electron beam.

6. The X-ray tomography device according to claim 1, wherein the processor is computing the 3D tomography image during a time period lower than an acquisition length of time used for producing the acquired images corresponding to all the images in the plurality of cell angles.

7. The X-ray tomography device according to claim 1, wherein the cell has a size comprised in the range of 0.3 cm to 20 cm.

8. The X-ray tomography device according to claim 1, wherein the casing of the cell is made of a material comprising beryllium, beryllium alloy, or a carbon-carbon composite.

9. The X-ray tomography device according to claim 1, wherein the photon detector comprises a CCD of at least ten megapixels.

10. The X-ray tomography device according to claim 1, further comprising a grating based interferometer situated between the cell and the photon detector.

11. The X-ray tomography device according to claim 1, further comprising a microscope situated between the cell and the photon detector.

12. The X-ray tomography device according to claim 3, wherein the outer casing is able to withstand to a pressure up to 1000 bars.

13. The X-ray tomography device according to claim 4, wherein the outer casing is able to withstand to a temperature up to 650° C.

14. The X-ray tomography device according to claim 5, wherein the X-ray source is a compact light source using a collision between a laser beam and an opposing electron beam.

15. The X-ray tomography device according to claim 1, wherein the cell has a size comprised in the range of 0.6 cm to 10 cm.

16. A method for providing a 3D tomography image of a sample from an X-ray tomography device, said method comprising:
    emitting a photon beam from an X-ray source in the direction of a beam axis at a cell adapted to include a porous sample to be imaged,
    positioning the cell inside the photon beam so that each acquired image produced by a photon detector comprises at least 70% of pixels corresponding to the sample
    rotating the cell about a cell angle around a cell axis that is substantially perpendicular to the beam axis,
    flooding the cell with at least one fluid,
    receiving a transmitted photon beam by the photon detector, said photon beam transmitted through said cell,
    providing said photon detector with at least one acquired image for each angle of a plurality of cell angles, and
    processing 3D tomography image on the basis of the acquired images corresponding to the plurality of cell angles,
    controlling an exposure length of time of the photon detector in the photon beam for each acquired image so as the exposure length of time is higher than a first time limit and lower than a second time limit, said first time limit being determined so as the pixels not corresponding to the sample are overexposed, and the second time limit being determined so as the pixels corresponding to the sample are not overexposed, and
    computing the 3D tomography image for a region of interest with the non overexposed pixels and with the overexposed pixels.

17. The method according to claim 16, wherein computing the 3D tomography image occurs during a time period lower than an acquisition length of time used for producing the acquired images corresponding to all the images in the plurality of cell angles.

18. The method according to claim 16 further comprising disposing a grating based interferometer between the cell and the photon detector.

19. The method according to claim 16, further comprising disposing a microscope between the cell and the photon detector.

20. The method according to claim 16, wherein the X-ray source is a compact light source using a collision between a laser beam and an opposing electron beam.

* * * * *